United States Patent [19]

Horng

[11] Patent Number: 4,981,651
[45] Date of Patent: Jan. 1, 1991

[54] APPARATUS FOR STERILIZING SHOES

[76] Inventor: Wen-Jenn Horng, No. 28, Ta-Ho Lane 1, Alley 1, Ta-Ho Li, Hsi-Tun Dist., Taichung, Taiwan

[21] Appl. No.: 466,568
[22] Filed: Jan. 17, 1990
[51] Int. Cl.⁵ .................. A61L 9/20; A01N 5/06
[52] U.S. Cl. ........................ 422/24; 422/300; 422/124; 34/104; 34/202; 250/492.1; 250/455.1
[58] Field of Search ............ 422/300, 24, 124; 34/104, 202; 250/492.1, 455.1

[56] References Cited
U.S. PATENT DOCUMENTS

| | | | |
|---|---|---|---|
| 1,639,753 | 8/1927 | Shelton | 250/492.1 |
| 2,350,091 | 5/1944 | Bergman | 422/24 |
| 2,699,771 | 1/1955 | Ruttger-Pelli | 128/393 |
| 3,078,526 | 2/1963 | Caruso | 34/104 |

Primary Examiner—Robert J. Warden
Assistant Examiner—Abanti B. Singla
Attorney, Agent, or Firm—Sughrue, Mion, Zinn, Macpeak and Seas

[57] ABSTRACT

An apparatus for sterilizing a shoe includes a housing 1 mounting an elongate ultraviolet lamp 2, a heating element 3 and a ventilating fan 4. Exposure of the inner sole of the shoe to the ultraviolet rays and the heated air has a sterilizing effect, thus stopping the growth of bacteria and fungi in the shoe. The apparatus may be designed to sterilize a pair of shoes at the same time, or it may have some flexible parts to allow it to reach the inner sole of other footwear such as boots and the like.

11 Claims, 9 Drawing Sheets

APPARATUS FOR STERILIZING SHOES

BACKGROUND OF THE INVENTION

This invention relates to an apparatus for sterilizing shoes, more particularly to an apparatus which stops the growth of bacteria and fungi in a shoe.

The main cause of most common foot diseases such as athlete's foot or dermatophytosis has been attributed to fungal or bacterial infection. As is well known, these fungi and bacteria thrive under cool and dark conditions, making an ordinary shoe an ideal incubator for such organisms.

Most people usually show no concern for the dangers of neglecting foot hygiene. Others may think that merely spraying disinfectant solution inside the shoe will eradicate the organisms, but this is not always the case. This is especially true when the shoe becomes damp due to rain water.

SUMMARY OF THE INVENTION

It is therefore an object of this invention to provide an apparatus for sterilizing a shoe by exposing the fungi and bacteria to a combination of heated air and ultraviolet rays.

Another object of this invention is to provide an apparatus for sterilizing a shoe which can fit a wide variety of shoes.

A final object of this invention is to provide an apparatus for sterilizing a shoe which is easy and simple to use.

Accordingly, an apparatus of this invention generally comprises a housing, an ultraviolet means, a heating element, and a ventilating means. To use this invention, the end with the ultraviolet means is simply inserted into the inner sole of the shoe before the electric power source is turned on. Using an apparatus of this invention would expose the bacteria and fungi not only to hot air, but also to ultraviolet rays, thus completely sterilizing the shoe.

BRIEF DESCRIPTION OF THE DRAWINGS

Other features of this invention will become apparent in the following detailed description of the preferred embodiments of this invention with reference to the accompanying drawings, in which.

DETAILED DESCRIPTION OF THE PREFERRED EMBODIMENTS

Figure 1:
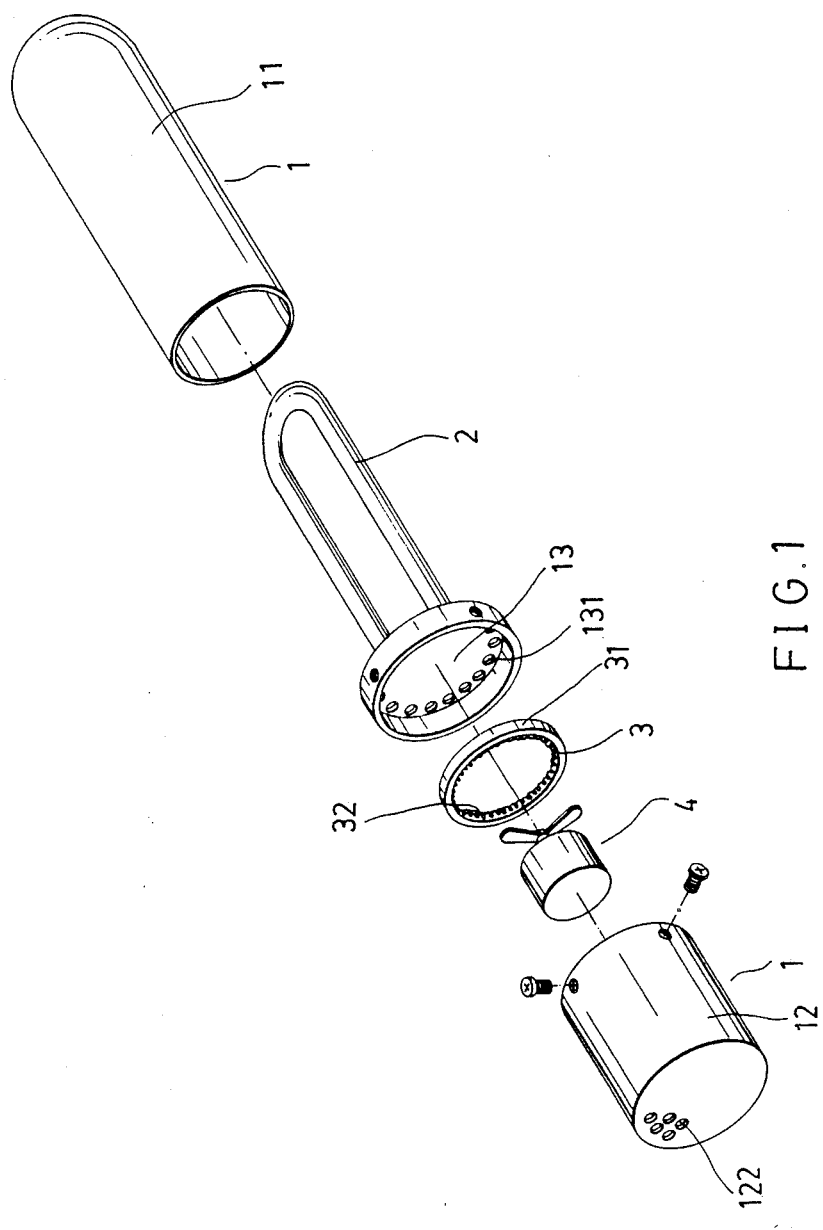
FIG. 1 is an exploded perspective view showing a preferred embodiment of an apparatus according to this invention.

Referring to FIG. 1, an exploded perspective view of a preferred embodiment of this invention is shown. The apparatus of this figure generally comprises an elongated housing 1 substantially shaped as a hollow closed cylinder, with a first base 13 separating the housing 1 into a casing 11 and a second housing base 12, which is formed as a chamber; an ultraviolet means 2, such as an ultraviolet lamp, shaped as a U-shaped tube having a front end and rear terminal ends, with the rear terminal ends received by receptacles 130 (FIG. 2) provided for in the first base 13; an electric heating element 3 mounted inside the second housing base 12; and an electric ventilating means 4 mounted at the closed end of the second housing base 12. The ultraviolet means 2 is covered by the casing 11, which has a transparent surface to allow ultraviolet rays from the ultraviolet means 2 to pass through the casing 11. The heating element 3, which is mounted between the ventilating means 4 and the ultraviolet means 2, has a base 31 which forms a ring around the inner surface of the wall of second housing base 12. A heating coil 32 is fixed along base 31. The base 31 is made of an insulating material, preferably ceramic, in order to prevent damage to housing 1 from heating element 3 due to overheating. The ultraviolet means 2, the heating element 3 and the ventilating means 4 are all powered by electric means.

Figure 2:
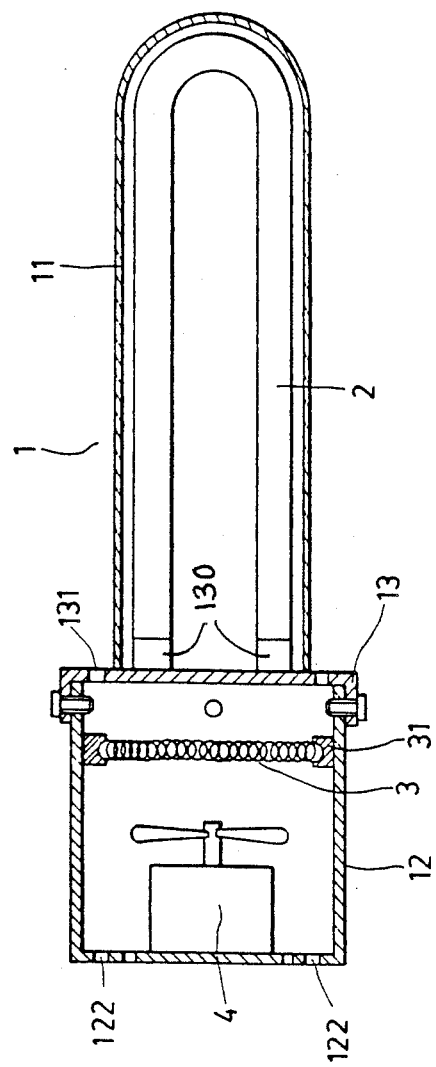
FIG. 2 is a sectional view of the embodiment shown in FIG. 1.

FIG. 2 is a sectional view of the preferred embodiment illustrated in FIG. 1. In this figure, the diameter of casing 11 is smaller than the diameter of second housing base 12. On first base 13, a group of holes 131 is formed around the base of casing 11. At the closed end of second housing base 12, another group of holes 122 is formed beside ventilating means 4 to serve as an air inlet for the ventilating means 4. The air inhaled by ventilating means 4 passes through the heating element 3 and exits through the holes 131 of the first base 13. The air serves to heat and dry the inner sole of the shoe, thus aiding in the sterilization process.

Figure 3:
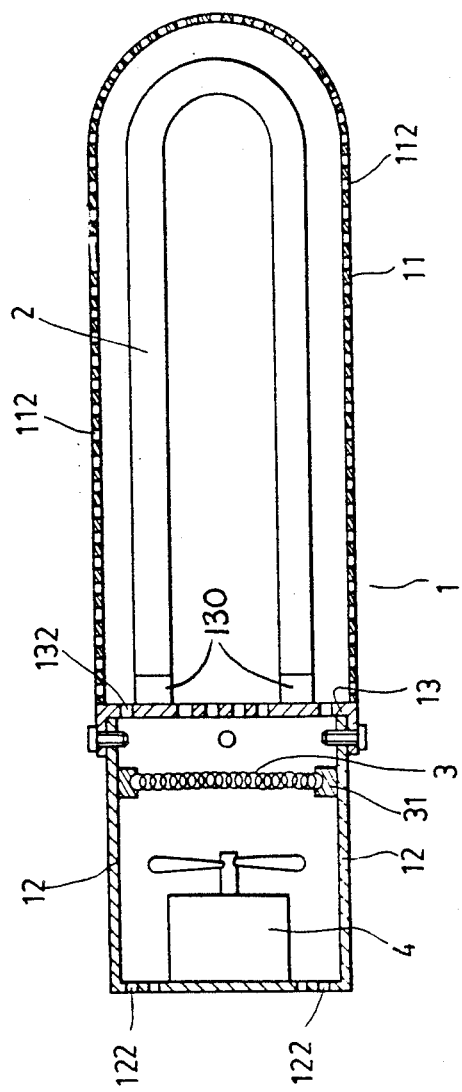
FIG. 3 illustrates a sectional view of a modification of the embodiment shown in FIGS. 1, 2.

FIG. 3 is a sectional view of a modification of the preferred embodiment shown in FIGS. 1, 2. The diameter of casing 11 is similar to the diameter of second housing base 12. The casing 11 further comprises a plurality of holes 112 along its entire surface. The first base 13 is perforated with holes 132. Air from holes 122 of second housing base 12 is directed by ventilating means 4 to pass through the heating element 3. The heated air then passes through holes 132 of the first base 13 and exits through holes 112 of casing 11.

Figure 4:
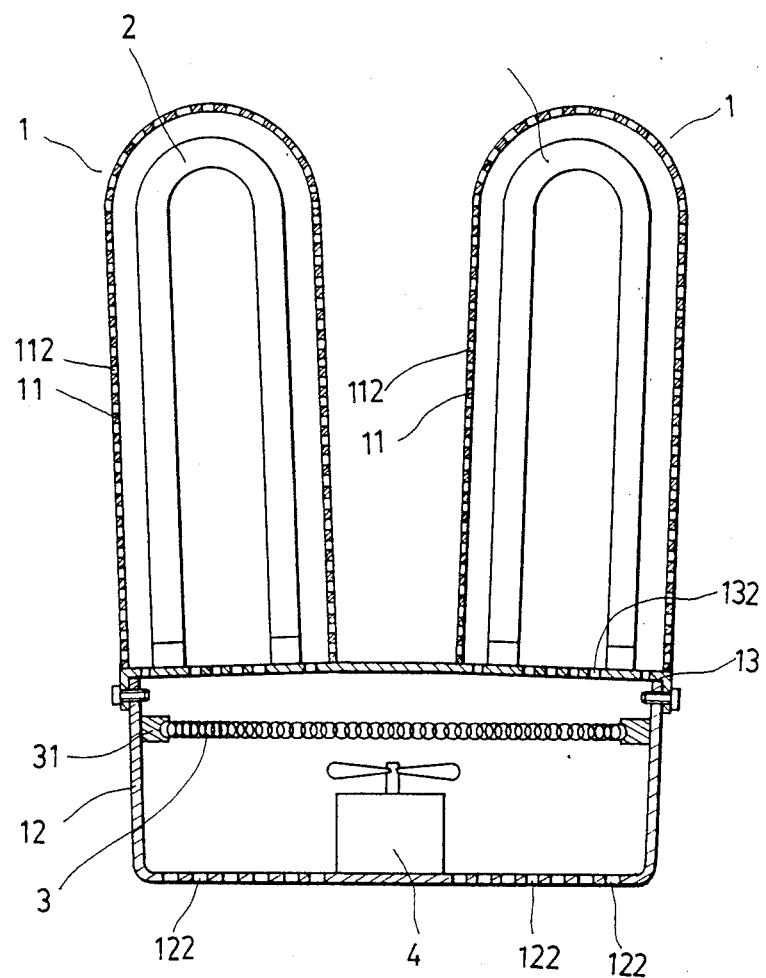
FIG. 4 shows a sectional view of a modification of the embodiment found in FIG. 3.

FIG. 4 shows a sectional view of a modification of the embodiment found in FIG. 3. In this figure, the first base 13 receives two ultraviolet means 2, each ultraviolet means 2 housed in the casing 11, which has holes 112 around its surface. The second housing base 12 and the two ultraviolet means 2 are formed in such a way that it is possible for the apparatus to be inserted into a pair of shoes.

Figure 5:
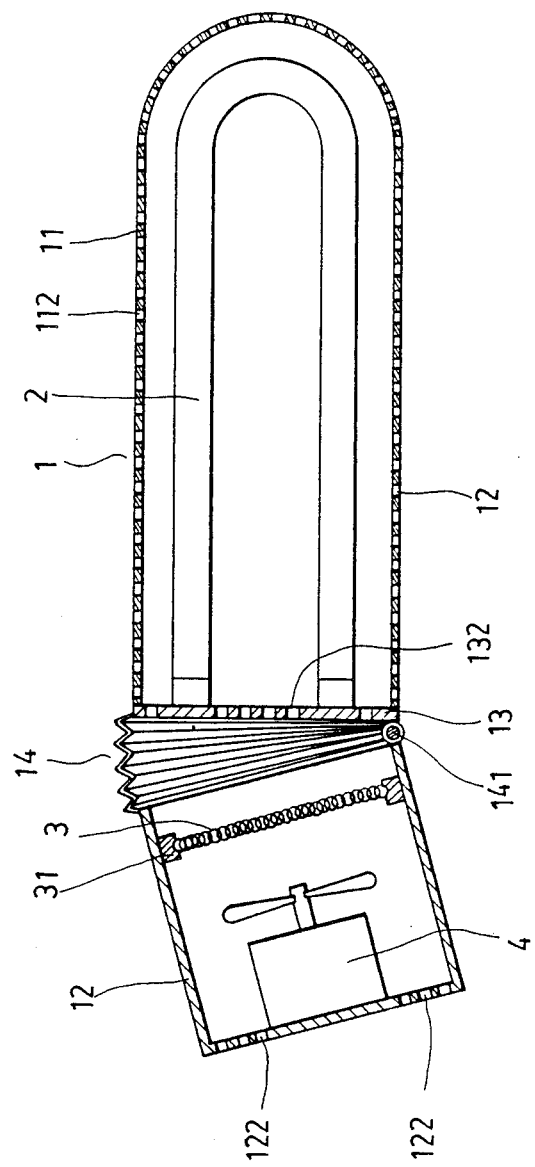
FIG. 5 illustrates a sectional view of another preferred embodiment according to this invention.

Since there are many kinds of shoes with different features available to the buying public, the apparatus will have to be modified to make it adaptable to a wide variety of shoe sizes and designs. FIG. 5 is a sectional view of a preferred embodiment which allows greater flexibility. In this figure, the embodiment shown in FIG. 4 has a bellows-like member 14 connecting second housing base 12 to the first base 13, serving as a path for the heated air. The bellows-like member 14 is fastened at one side by a joint 141, rotatably linking the first base 13 to the second housing base 12. The action of bellows-like member 14 allows casing 11 to bend away from second housing base 12 or vice versa, in a direction within a certain angular range governed by the length of the bellows-like member 14, enabling the casing 11 to easily reach the inner sole of different types of shoes.

Figure 6:
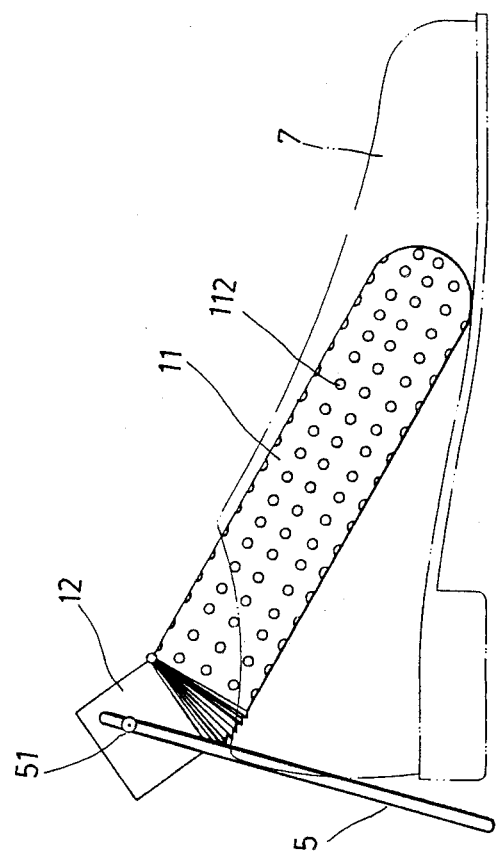
FIG. 6 is a side view of a modification of the embodiment of FIG. 5 in use.

FIG. 6 illustrates the use of the preferred embodiment found in FIG. 5. A supporting member 5 may be rotatably joined to second housing base 12 through a joint 51 to allow the apparatus to stand on its own.

Figure 7:
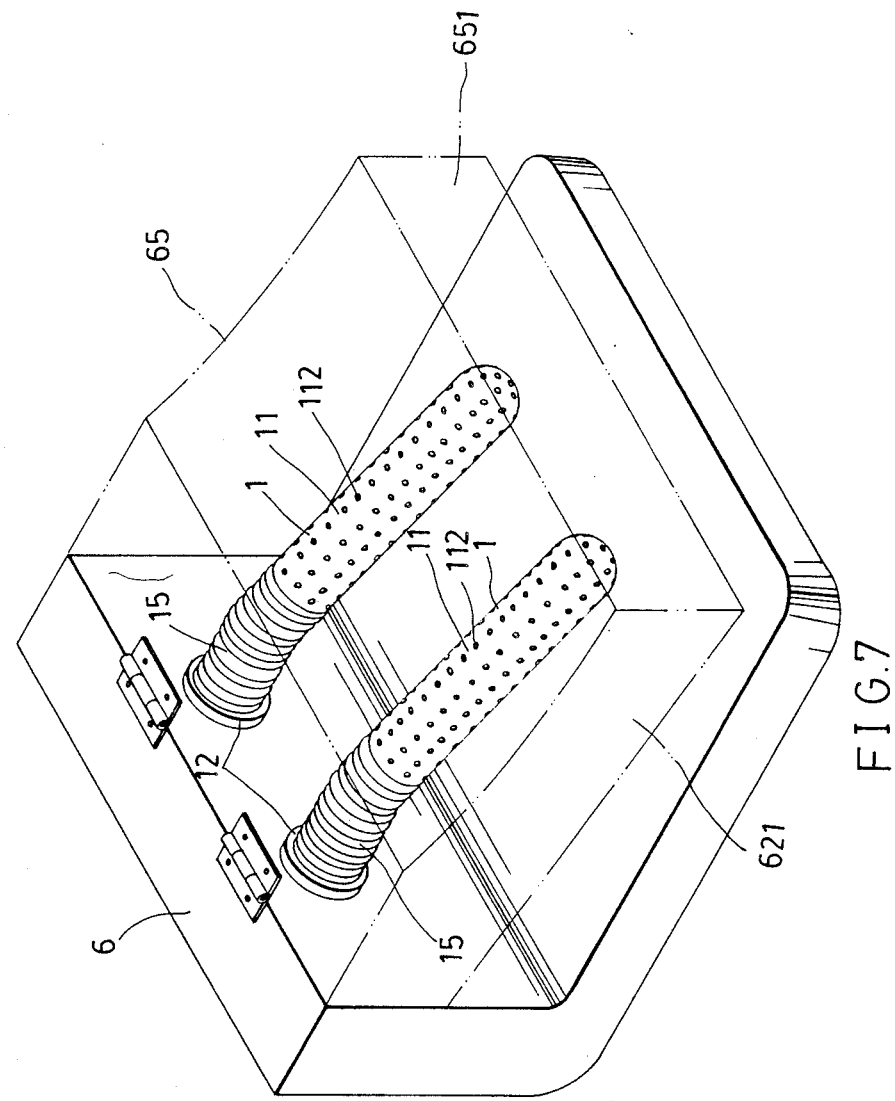
FIG. 7 illustrates a perspective view of still another preferred embodiment according to this invention.

FIG. 7 shows a perspective view of another preferred embodiment of this invention. In this figure, two ultraviolet means are provided to make it possible to sterilize a pair of shoes at the same time. The two first bases 13 are connected to second housing base 12 through flexible bellows-like members 15. The second housing base 12 is substantially L-shaped such that it can be placed on a horizontal surface.

Figure 8:
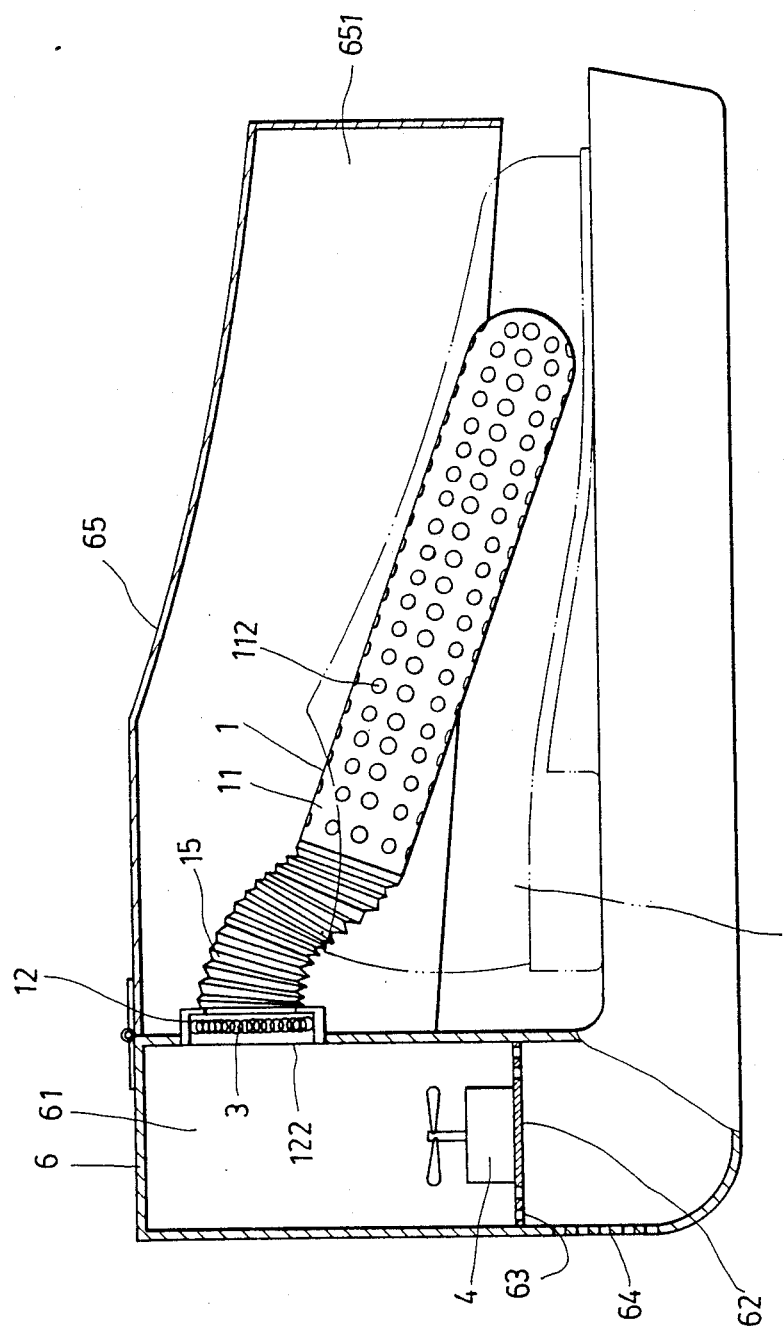
FIG. 8 is a sectional view of the embodiment shown in FIG. 7.

Referring to FIG. 8, the heating element 3 is mounted on the portion of second housing base 12 at the internal side wall of hollow body 6. A flat horizontal partition 62 with a plurality of holes 63 is formed inside hollow body 6, thus separating the hollow space into two areas. The ventilating means 4 is mounted on the flat partition 62. On the external wall of hollow body 6, a short distance below the flat partition 62 is a plurality of holes 64. Thus, the air flows in this manner: the air first enters the holes 64 on the external wall, then passes through the holes 63 of the flat partition 62, is inhaled by the ventilating means 4, passes through the heating element 3, into the flexible bellows-like member 15 and finally exits through the holes 112 of casing 11.

When using the apparatus shown in this figure, a shoe is placed on the base of the hollow body 6. The casing 11, which is movable due to flexible bellows-like member 15, is then placed inside the inner sole of the shoe to be sterilized. The electric means, which is not shown in the figure, is turned on.

To obtain better results, a shield 65 with a folded edge 651 is hinged to the top edge of the external side wall of the hollow body 6, shielding the portion above the base of said hollow body 6. The shield 65 makes it possible for the apparatus to retain the heated air for a longer period of time so it can be used in drying wet shoes.

Figure 9:
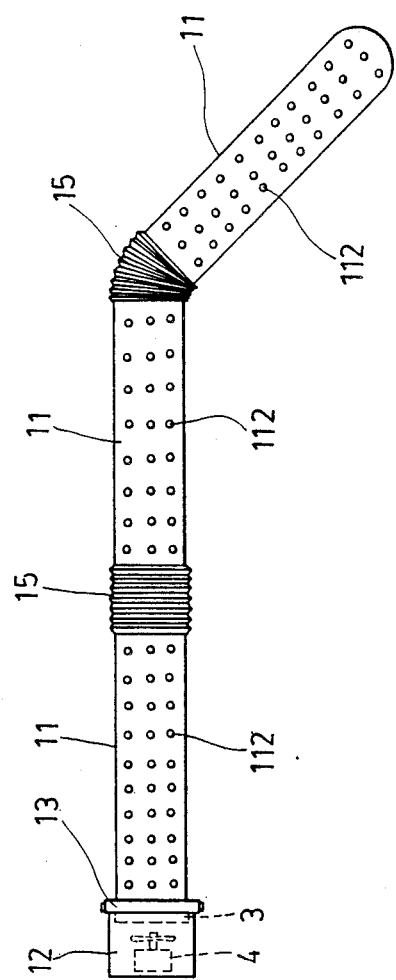
FIG. 9 shows a side view of a further preferred embodiment according to this invention.

FIG. 9 shows a side view of still another preferred embodiment of this invention. The apparatus comprises a plurality of casings 11 connected to one another by flexible bellows-like members 15. An ultraviolet means 2 is housed within each of the casings 11. The embodiment of this figure can be used in boots and the like.

While the present invention has been described in connection with what are considered the most practical and preferred embodiments, it is understood that the invention is not limited to the disclosed embodiments, but is intended to cover various arrangements included within the spirit and scope of the broadest interpretation, so as to encompass all such modifications and equivalent arrangements.

I claim:
1. An apparatus for sterilizing shoes comprising:
   at least one ultraviolet means having a front end and two rear terminal ends;
   a first base including a plurality of first perforations, and receptacles for receiving the rear terminal ends of said ultraviolet means;
   a second housing base having a chamber therein and a plurality of air inlet perforations,
   means for joining said second housing base to said first base;
   an electric ventilating means mounted inside said chamber for drawing in air from the air inlet perforations of said second housing base and directing such air towards the front end of said ultraviolet means;
   at least one electric heating element mounted inside said chamber between said ultraviolet means and said ventilating means; and
   a casing attached to said first base to serve as a cover for each of said ultraviolet means, wherein the diameter of said first base is larger than that of said casing, creating an annular step portion between said first base and said casing, said first perforations being formed on said annular step portion.

2. The apparatus as claimed in claim 1, wherein a plurality of holes are formed in a wall of said casing to enable the air drawn in by said ventilating means to pass through said casing.

3. The apparatus as claimed in claim 1, wherein said second housing base is a hollow member having a closed end and an open end, said open and being closed by said first base.

4. The apparatus as claimed in claim 3, further comprising a bellows-like flexible member interconnecting said first base and said open end of said second housing base.

5. The apparatus as claimed in claim 4, further comprising a supporting member rotatably joined to said second housing base.

6. The apparatus as claimed in claim 1, further comprising a bellows-like member interconnecting said first base and said second housing base.

7. The apparatus as claimed in claim 6, wherein said second housing base has a first outer wall opposite to said first base and a second outer wall extending longitudinally with respect to said ultraviolet means, said first outer wall being connected to said bellows-like member and having an opening communicated with said bellows-like member.

8. The apparatus as claimed in claim 7, further comprising an elongate shield coupled at one end by a hinge to said first outer wall of said second housing base and covering said casing of said ultraviolet means.

9. The apparatus as claimed in claim 1, wherein said casing is made of a transparent material.

10. The apparatus as claimed in claim 1, wherein said heating element comprises:
    an insulating base having an outer peripheral surface attached to an internal surface of said second housing base; and
    a heating coil fixed along said insulating base.

11. An apparatus for sterilizing shoes comprising:
    at least one elongate ultraviolet means having a front end and two rear terminal ends;
    a first base including a plurality of first perforations, and receptacles for receiving the rear terminal ends of said ultraviolet means;
    a second housing base having a chamber therein and a plurality of air inlet perforations,
    means for joining said second housing base to said first base;
    an electric ventilating means mounted inside said chamber for drawing in air from the air inlet perforations of said second housing base and directing such air through said first perforations towards the front end of said ultraviolet means;

at least one electric heating element mounted inside said chamber between said ultraviolet means and said ventilating means; and a casing attached to said first base, surrounding said first perforations, and serving as a cover for said ultraviolet means, wherein a plurality of holes are formed in a wall of said casing to enable the air directed through said first perforations by said ventilating means to pass through said casing.

* * * * *